United States Patent

Xu et al.

[11] Patent Number: 5,852,198
[45] Date of Patent: Dec. 22, 1998

[54] WITTIG REAGENTS AND METHOD FOR PREPARING α,β-UNSATURATED PHOSPHONATES

[75] Inventors: Yibo Xu, Chicago; Michael T. Flavin, Darien, both of Ill.

[73] Assignee: Medichem Research, Inc., Lemont, Ill.

[21] Appl. No.: 831,233

[22] Filed: Apr. 2, 1997

Related U.S. Application Data

[60] Provisional application No. 60/014,764 Apr. 3, 1996.

[51] Int. Cl.$^6$ ........................................................ C07F 9/54
[52] U.S. Cl. ............................................ 558/87; 558/155
[58] Field of Search ........................................ 558/87, 155

[56] References Cited

U.S. PATENT DOCUMENTS

| | | | |
|---|---|---|---|
| 3,662,031 | 5/1972 | Moffatt et al. | 558/155 X |
| 4,740,608 | 4/1988 | Phillion | 558/45 |
| 5,250,522 | 10/1993 | De Lombaert | 514/114 |
| 5,491,134 | 2/1996 | Sher et al. | 514/114 |

FOREIGN PATENT DOCUMENTS

| | | |
|---|---|---|
| 20 09 834 | 9/1970 | Germany. |
| 1 243 214 | 8/1971 | United Kingdom. |

OTHER PUBLICATIONS

File CAPLUS on STN®, Chemical Abstracts Service, (Columbus, Ohio), Accession No. 1971:54150, DE 2009834, 1971.
Engel, R. *Chem Rev.* 1977, 77, 349.
Blackburn G. M.; Perree, T. D.; Rashid, A.; Bisbal, C.; Lebleu, B. *Chem. Scr.* 1986, 26, 21.
O'Donnell, M. J.; Lawley, L. K.; Pushpavanam, P. B.; Burger, A.; Bordwell, F. G.; Zhang, X.– M. *Tetrahedron Lett.* 1994, 35, 6421 and references cited therein.
Minami, T.; Motoyoshiya, J. *Synthesis* 1992, 333.
Jones, G. H.; Hamamura, E. K.; Moffatt, J. G. *Tetrahedron Lett.* 1968, 5731.
Jones, G. H.; Moffatt, J. G. *J. Am. Chem. Soc.* 1968, 90, 5337.
Fuertes, M.; Witkowski, J. T.; Streeter, D. G.; Robins, R. K. *J. Med. Chem.* 1974, 17, 642.
Kappler, F.; Hai, T.T.; Cotter, R. J.; Hyver, K. J.; Hampton, A. *J. Med. Chem.* 1986, 29.
Martin, J. C.; Verheyden, J. P. H. *Nucleosides Nucleotides* 1988, 7, 365.
Secrist, J. A., III; Riggs, R. M.; Comber, R. N.; Montgomery, J. A. *Nucleosides Nucleotides* 1992, 11, 947.
Freeman, G. A.; Rideout, J. L.; Miller, W. H.; Reardon, J. E. *J. Med. Chem.*, 1992, 35, 3192.
Gupta, A.; Sacks, K.; Khan, S.; Tropp, B. E.; Engel, R. *Synthetic Commun.* 1980, 10, 299.
Phillion, D. P.; Andrew, S. S. *Tetrahedron Lett.* 1986, 27, 1477.
Creary, X.; Underiner, T. L. *J. Org. Chem.* 1985, 50, 2165.
Holy, A.; Rosenberg, I. *Coll. Czech. Chem. Commun.* 1982, 47, 3447.
Krecmerova, M.; Hrebabecky, H.; Holy, A. *Coll. Czech. Chem. Commun.* 1990, 55, 2521.
Kenyon, G. L.; Westheimer, F. H. *J. Am. Chem. Soc.* 1966, 88, 3557.
Petrov, A. A.; Ionin, B. I.; Ignatyev, V. M. *Tetrahedron Lett.* 1968, 15.
Tavs, P.; Weitkamp, H. *Tetrahedron* 1970, 26, 5529.
Xu, Y.; Flavin, M.T.; Xu, Z. *Journal of Organic Chemistry* 1996, 61, 7697.
Kafarski, P.; Lejczak, B. *Phosphorus, Sulfur, Silicon, Relat. Elem.* 1991, 63, 193.
Wadsworth, W. S., Jr. *Org. React.* 1977, 25, 73.
Maryanoff, B. E.; Reitz, A. B. *Chem. Rev.* 1989, 89, 863.
Bhattacharya, A.; Thyagarajan, G. *Chem. Rev.* 1981, 81, 415.
Stang, P. J.; Hanack, M.; Subramanian, L. R. *Synthesis* 1982, 85.
Krishnakumar, V.K., Sharma, M.M. *Synthesis*, Jul. 1983, 558.
Xu, Y.; jin, X.; Huang, G.; Huang, Y. *Synthesis* 1983, 556.

*Primary Examiner*—Michael G. Ambrose
*Attorney, Agent, or Firm*—McDonnell Boehnen Hulbert & Berghoff

[57] ABSTRACT

Wittig-type reagents and methods of preparation and use thereof for preparing α,β-unsaturated phosphonate esters from aldehydes and ketones are disclosed. The Wittig-type reagents have the following formulae:

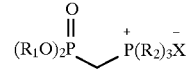

I

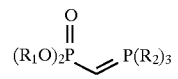

II wherein X represents triflate, halide, BF$_4$, SbF$_6$, or ClO$_4$; R$_1$ represents alkyl, aryl or arylalkyl; and R$_2$ represents alkyl, aryl or arylalkyl, provided that R$_1$ and R$_2$ not represent phenyl at the same time. The Wittig reagent diethyl phosphono-methylidenetriphenylphosphorane (1b) has been successfully synthesized for the first time via its phosphonium triflate salt (4a), by treating diethyl phosphonomethyltriflate with triphenylphosphine according to the disclosed method. The procedure has been applied to the synthesis of other new Wittig-type reagents such as phosphoranes and phosphonium salts. The new Wittig reagents thus synthesized were treated with various aldehydes and an activated ketone, affording the corresponding α,β-unsaturated phosphonates, saturated phosphonates or phosphoric acids. Triphenylphosphorane 1b and triphenylphosphonium 4a led to both cis and trans isomers with the latter being predominant, while trans isomers were almost exclusively formed when tributyl reagents (1c and 4d) were used.

6 Claims, No Drawings

WITTIG REAGENTS AND METHOD FOR PREPARING α,β-UNSATURATED PHOSPHONATES

CROSS-REFERENCE

This application is a continuation-in-part of Provisional Application Ser. No. 60/014,764, filed Apr. 3, 1996.

FIELD OF THE INVENTION

The present invention relates to novel Wittig-type reagents and methods for preparation and use thereof for preparing α,β-unsaturated phosphonates and their saturated phosphonates and phosphoric acid analogues thereof. The work described in this application was supported, in part, by a Phase I Small Business Innovation Research (SBIR) Grant (1R43 AI38205) from the National Institutes of Health. The U.S. Government may have certain rights to this invention.

BACKGROUND OF THE INVENTION

Phosphonic acids have been frequently used as suitable isosteric and isoelectronic replacements for biologically important phosphates such as nucleotides, phospholipids, nucleoside polyphosphates, and sugar phosphates.[1,2] Also, phosphonic acids containing an amino group in the α-, β-, or γ-position have attracted considerable interest as replacements for natural amino acids.[3,4] These phosphonic acid analogues can exert their biological activity as regulators, mediators, or enzyme inhibitors.[1–4] In addition, phosphonates have found wide application in general organic synthesis.[5–7] For example, phosphonate-stabilized carbanions undergo Homer-Wadsworth-Emmons condensation with aldehydes and ketones to afford olefins;[5,6] vinyl phosphonates have been used in Diels-Alder reactions and Michael additions, and they are also versatile intermediates for the synthesis of hetero- and carbocyclic compounds.[7]

Numerous methods have been reported in the literature for the synthesis of phosphonates, the best known of which are the Arbuzov and Michaelis-Becker reactions.[8] The Wittig reagent, diphenyl phosphonomethylidenetriphenylphosphorane 1a, [(RO)$_2$P(O)CH=PPh$_3$ where R=Ph], developed by Moffatt, et al. in 1968[9] has been applied to the synthesis of various diphenyl phosphonates.[5,6,10–15] However, the subsequent removal of the phenyl groups is difficult and requires either transesterification of the diphenyl ester into the dibenzyl ester followed by hydrogenolysis, or alkaline hydrolysis to remove one phenyl group followed by enzymatic treatment with Crotalus atrox phosphodiesterase to remove the second one.[10–15] Moffat, et al. had attempted to prepare the reagent diethyl phosphonomethylidenetriphenylphosphorane 1b [(RO)$_2$P(O)CH=PPh$_3$ where R=Et] by reaction of triphenylphosphine with diethyl iodomethylphosphonate, but were not successful.[9]

Tetraethyl methylenebisphosphonate (2) [(Et)$_2$P(O)CH$_2$P(O)(OEt)$_2$] has been used in Homer-Wadsworth-Emmons condensations to provide diethyl phosphonates,[5,6] which can be readily hydrolyzed by using Me$_3$SiBr. Strongly basic reagents are generally required for such condensations and, therefore, may not be suitable for base-sensitive aldehydes and ketones, resulting in poor yield and the formation of side products.[16]

Accordingly, while methods for preparing phosphonates and derivatives thereof are known, there is a need in the art for improved methods for preparing α,β-unsaturated phosphonates, saturated phosphonates and phosphoric acids from aldehydes and ketones under mild conditions.

SUMMARY OF THE INVENTION

The present invention provides new Wittig-type reagents and methods for preparation and use thereof for preparing α,β-unsaturated phosphonate esters from a phosphonium triflate under less basic conditions and executing the subsequent hydrolysis under mild conditions. The Wittig-type reagents of the invention having the following formulae:

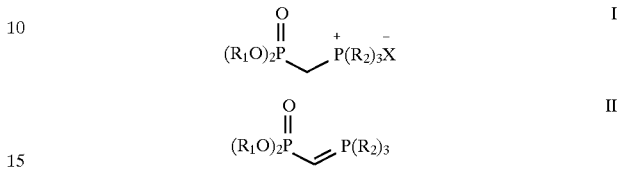

wherein X represents triflate, halide, BF$_4$, SbF$_6$, ClO$_4$; R$_1$ represents alkyl, aryl or arylalkyl; and R$_2$ represents alkyl, aryl or arylalkyl, provided that R$_1$ and R$_2$ not represent phenyl at the same time.

Trifluoromethanesulfonate (triflate) is an excellent leaving group and has been widely used in organic synthesis.[17] The Applicants discovered that reaction of dialkyl (aryl, alkyl, or arylalkyl)phosphonmethyltriflate, e.g., diethyl phosphonomethyltriflate (3a), readily reacts with triphenylphosphine to form a dialkyl (aryl, alkyl or arylalkyl) phosphonium methyltriflate such as phosphonium triflate salt 4a, which, in turn, yields the ylide 1b after treatment with a base. Ylide 1b can be used for the synthesis of α,β-unsaturated phosphonate esters as well their corresponding saturated phosphonate ester and phosphoric acid derivatives. Thus, the Wittig reagent diethyl phosphonomethylidenetriphenylphosphorane (1b) has been successfully synthesized for the first time using the inventive method. Scheme 1 below illustrates the method of the invention.

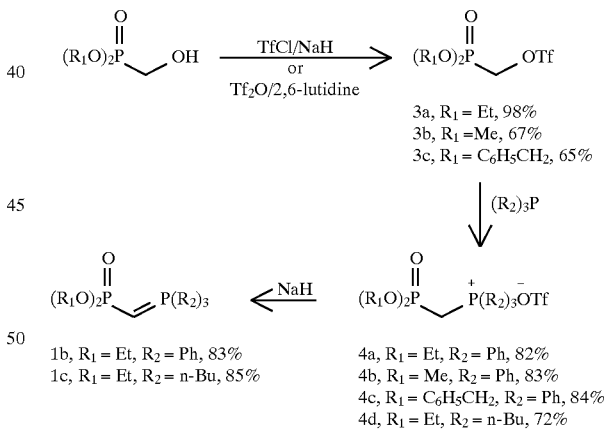

Scheme 1

3a, R$_1$ = Et, 98%
3b, R$_1$ = Me, 67%
3c, R$_1$ = C$_6$H$_5$CH$_2$, 65%

1b, R$_1$ = Et, R$_2$ = Ph, 83%
1c, R$_1$ = Et, R$_2$ = n-Bu, 85%

4a, R$_1$ = Et, R$_2$ = Ph, 82%
4b, R$_1$ = Me, R$_2$ = Ph, 83%
4c, R$_1$ = C$_6$H$_5$CH$_2$, R$_2$ = Ph, 84%
4d, R$_1$ = Et, R$_2$ = n-Bu, 72%

DETAILED DESCRIPTION OF THE INVENTION

All literature, patents, and patent applications cited herein are hereby incorporated by reference in their entirety. The present invention relates to new Wittig-type reagents and methods for preparation and use thereof for preparing α,β-unsaturated phosphonate esters, saturated phosphonate esters and phosphoric acids from a phosphonium triflate under less basic conditions and executing the subsequent hydrolysis under mild conditions. The Wittig-type reagents of the invention having the following formulae:

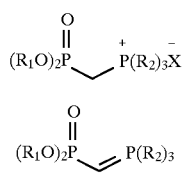

$$(R_1O)_2P\overset{O}{\underset{\|}{}}\diagdown P(R_2)_3 X^- \quad \text{I}$$

$$(R_1O)_2P\overset{O}{\underset{\|}{}}\diagdown P(R_2)_3 \quad \text{II}$$

wherein X represents triflate, halide, $BF_4$, $SbF_6$, $ClO_4$; $R_1$ represents alkyl, aryl or arylalkyl; and $R_2$ represents alkyl, aryl or arylalkyl, provided that $R_1$ and $R_2$ not represent phenyl at the same time. As defined herein, alkyl refers to branched or linear $C_{1-6}$; aryl refers to phenyl or substituted phenyls including mono, di, and trisubstituted phenyls such as 4-methoxyphenyl and 4-chlorophenyl; and arylalkyl includes phenylalkyls and substituted phenylalkyls which include benzyl, triphenylmethyl, 4-methoxytriphenyhnethyl, and 4,4'-dimethoxy-triphenylmethyl. In the preferred embodiments, $R_1$ represents methyl, ethyl, or benzyl and $R_2$ represents n-butyl or phenyl for formula I and $R_1$ represents ethyl and $R_2$ represents n-butyl or phenyl for the formula II compounds.

As shown above in Scheme 1, two methods have been published for the synthesis of diethyl phosphonomethyltriflate (3a) from diethyl hydroxymethylphosphonate, one of which used triflic chloride in the presence of sodium hydride,[18] while the other employed triflic anhydride and lutidine.[19] The second procedure is preferred for the preparation of 3a because triflic anhydride is less volatile than triflic chloride and, thus, is relatively easier to handle. Representative dialkyl phosphonomethyltriflates, dimethyl and dibenzyl phosphonomethyltriflate (3b and 3c), were also prepared by the same procedure from the corresponding hydroxyl compounds (Scheme 1).

with 3a, leading to the formation of 4d. Not surprisingly, diethyl phosphonomethyltosylate[20,21] failed to react with triphenylphosphine.

If desired, the triflate counterion of the phosphonium triflate salt of Formula I such as 4a–4c can be exchanged for other counter-anions such as halides, $BF_4$, $SbF_6$, and $ClO_4$ by reacting the formula I compound with the corresponding alkali-metal salts such as NaF, $NaBF_4$, $NaSbF_6$, or $NaClO_4$ in an appropriate solvent such as acetonitrile, methylene chloride or acetone. Methods for effecting counter-anion exchange are described for instance in Banks, R. E.; Besheesh, M. K. J Fluorine Chem., 1996, 76, 161 and Umemoto, T.; Tomita, K. Tetrahedron Lett., 1986, 27, 3271.

Treatment of 4a with aqueous NaOH led only to the isolation of triphenylphosphine oxide; however, treatment of 4a and 4d with sodium hydride in THF followed by non-aqueous work-up afforded the desired ylide 1b and 1c (Scheme 1). All the phosphonium triflate salts (4a–4d), as well as the ylides (1b and 1c), yielded satisfactory analytical and spectral data and were determined to be stable upon storage at room temperature.

The triphenylphosphonium triflate salt 4a and ylide 1b both proved to react smoothly with a variety of aromatic and aliphatic aldehydes at about 100° C. to generate α,β-unsaturated phosphonates (5a–5f). These results are presented in Table 1. In the reactions with triphenylphosphonium triflate salt 4a, triethylamine was added as a base and ylide 1b was assumed to be generated in situ. The presence of electron withdrawing groups accelerated the reaction while electron donating substituents slowed the reaction (entry 2 and 6, Table 1).

TABLE 1

The Reaction of Phosphonium Triflate Salts and Ylides with Aldehydes[a]

| Entry | Witting Reagents | Aldehyde | Time (h) | Yield[b] (%) | Product (ratio of trans: cis[c]) |
|---|---|---|---|---|---|
| 1 | 4a | PhCHO | 20 | 75 | PhCH=CHP(O)(Oet)$_2$ (5a)(70:30) |
| 2 | 4a | 4-Cl—PhCHO | 18 | 78 | 4-Cl-PhCH=CHP(O)(OEt)$_2$ (5b) (70:30) |
| 3 | 1b | 4-Cl—PhCHO | 4 | 68 | 5b (86:14) |
| 4 | 4d | 4-Cl—PhCHO | 6 | 72 | 5b (96:4) |
| 5 | 1c | 4-Cl—PhCHO | 6 | 78 | 5b (100:O) |
| 6 | 4a | 4-MeO—PhCHO | 40 | 50 | 4-MeO-PhCH=CHP(O)(OEt)$_2$ (5c) (80:20) |
| 7 | 4a | trans-PhCH=CHCHO | 20 | 57[d] | Ph(CH=CH)2P(O)(OEt)$_2$ (5d) (60:40) |
| 8 | 4a | PhCH$_2$CHO | 6 | 78 | PhCH=CHCH$_2$P(O)(OEt)$_2$ (5e) (100:0) |
| 9 | 1b | PhCH$_2$CHO | 4 | 68 | 5e (100:0) |
| 10 | 4a | CH$_3$(CH$_2$)$_3$CHO | 6 | 31[e] | CH$_3$(CH$_2$)$_3$CH=CHP(O)(OEt)$_2$ (5f) (75:25) |
| 11 | 4a | 4-Cl—PhCOCF$_3$ | 20 | 34 | 4-Cl-PhC(CF$_3$)=CHP(O)(OEt)$_2$ (5g) (75:25)[f] |
| 12 | 4d | 4-Cl—PhCOCF$_3$ | 16 | 34 | 5g (75:25)[f] |

[a]See the experimental section for detailed reaction conditions.
[b]In all the reactions, the starting aldehydes had not been completely consumed and were recovered.
[c]The isomers refer to the newly formed double bond and were deterrnined by 1H NMR.
[d]The two isomers (trans and cis) were separated by silica gel column chromatography and the yield was the combined one.
[e]Some products might be lost during the purification.
[f]The ratio of Z/E-isomers.

As designed, all the triflates (3a–3c) reacted readily with triphenylphosphine in $CH_2Cl_2$ at room temperature to afford phosphonium triflate salts 4a–4c in ca. 80% yield (Scheme 1). Tributylphosphine has also been demonstrated to react In contrast to the reaction of diphenyl phosphonate ylide 1a, in which only trans α,β-unsaturated phosphonates were observed,[9] a mixture of cis and trans isomers were formed with both phosphonium triflate salt 4a and ylide 1b and the ratios of trans/cis varied from 60:40 to 80:20. However, when suitably protected nucleoside aldehydes such as the 2',3'-isopropylideneadenosine derivative[10] were treated with ylide 1b at room temperature only trans isomer 6 was formed (Scheme 2). This result was similar to that observed for the diphenyl phosphonate ylide 1a.[10] Similarly, tributylphosphonium triflate salt 4d and the corresponding ylide 1c also reacted with aldehydes (entry 4 and 5, Table 1), but they appeared to be more reactive when compared with 4a and 1b, thereby requiring mild reaction conditions and resulting in formation of a higher percentage of trans isomer. For example, in the reaction of tributylphosphorane 1c with 4-chlorobenzaldehyde (entry 5, Table 1) the trans isomer of 5b was exclusively produced.

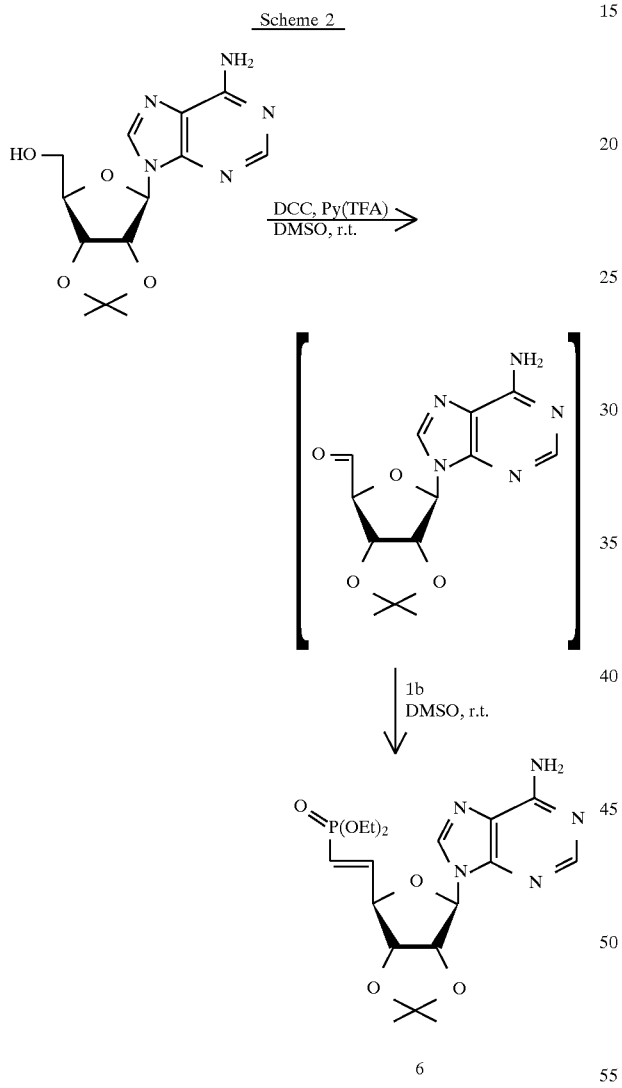

Reaction with ordinary ketones such as acetophenone was very slow under similar conditions with both phosphonium triflate salts (4a and 4d) and ylides (1b and 1c). However, activated ketones such as 4-chloro-2,2,2-trifluoroacetophenone reacted with both phosphonium triflate salts (4a and 4d) to afford the corresponding α,β-unsaturated phosphonate 5g, with the two isomers being formed in approximately a 75:25 ratio (entry 11 and 12, Table 1).

The structural assignments of the trans and cis isomers of 5a–5f were made by analysis of $^1$H NMR data. It is well established that the coupling constants between the olefinic protons and phosphorus in α,β-unsaturated phosphonates are within the following range: $J_{cis-H,H}$=8–15 Hz, $J_{trans-H,H}$=14–18 Hz, $J_{cis-H,P}$=10–30 Hz, $J_{trans-H,P}$=30–50 Hz, and $J_{geminal-H,P}$=12–20 Hz.[22-24] In the cases of 5a–5c, the signals due to the olefinic protons β to phosphorus overlapped with the phenolic protons, while the olefinic protons α to phosphorus had $J_{cis-H,H}$=$J_{geminal-H,P}$=ca. 15 Hz and $J_{trans-H,H}$=$J_{geminal-H,P}$=17–18 Hz.

For compound 5d, derived from trans-cinnamaldehyde, the two isomers (trans and cis in terms of the newly formed double bond) were separated by silica gel column chromatography and the cis isomer was unambiguously assigned due to its $J_{trans-H,P}$=50.7 Hz, and hence $J_{cis-H,H}$ being 12.5 Hz and $J_{geminal-H,P}$ being 17.4 Hz. Also, the two olefinic protons for both isomers of 5f were clearly assigned, since there was no interference with the phenolic protons. Thus, $J_{cis-H,H}$=13.0 Hz, $J_{trans-H,P}$=53.0 Hz, and $J_{geminal-H,P}$=19.9 Hz were observed for the cis isomer, while $J_{trans-H,H}$=17.1 Hz, $J_{cis-H,P}$=22.0 Hz, and $J_{geminal-H,P}$=21.2 Hz were found for the trans isomer.

Interestingly, compound 5e, the pure trans isomer, was the double bond-migrated product, in which the double bond was conjugated with the phenyl ring (β,γ-unsaturated phosphonate), instead of the normal α,β-unsaturated phosphonate. It might be hypothesized that the latter compound was originally formed in the reaction, but then rearranged to 5e under the reaction conditions (Scheme 3), suggesting that 5e is more thermodynamically stable. In the $^1$H NMR spectrum of 5e, neither geminal nor vicinal coupling between the two olefinic protons and phosphorus were observed. Instead, only long range coupling of the two olefinic protons from phosphorus were recorded, with the J values being 7.2 and 5.1 Hz, respectively. However, a typical geminal splitting by phosphorus was observed for the methylene group ($J_{geminal-H,P}$=22.2 Hz in $^1$H NMR and $^1J_{C,P}$=140.9 Hz in $^{13}$C NMR), confirming that the CH$_2$ group was attached to phosphorus. Hydrogenation of 5e led to the saturated phosphonate 7a (Scheme 3).

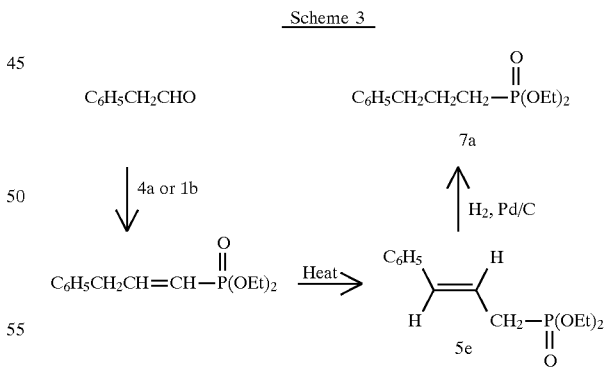

The resulting α,β-unsaturated phosphonate esters such as 5a–5d, and 5f produced by the method of the present invention can be hydrogenated to afford the saturated phosphonate esters or be easily hydrolyzed by Me$_3$SiBr to the corresponding phosphonic acids, examples of which are depicted in Scheme 4. The phosphonic acid 8 was a mixture of trans and cis isomers and the ratio was determined to be ca. 65:35 by $^1$H NMR, which was very similar to that of the starting ester 5b (70:30).

Scheme 4

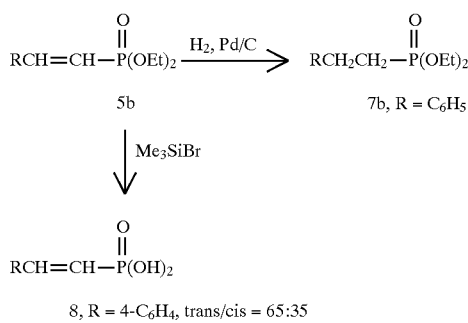

8, R = 4-C$_6$H$_4$, trans/cis = 65:35

In conclusion, various phosphonate Wittig reagents have been successfully synthesized and demonstrated to react with aldehydes and activated ketones under mild conditions. These reagents will find general application to the synthesis of α,β-unsaturated as well as saturated phosphonates and the corresponding phosphonic acids. The following Examples describe general procedures for preparing dialkyl phosphonomethyltriflates and generating the corresponding dialkyl phosphanomethylidenephosphorane ylides and use thereof for preparing the corresponding α,β-unsaturated phosphorane esters. The methods were applied in synthesizing a 2',3'-isopropylideneadenosine derivative as shown in Scheme 2.

EXAMPLES

The following examples are illustrative and do not serve to limit the scope of the invention as claimed. Chemical shifts are reported in parts per million (δppm) downfield from TMS, which was used as an internal standard. Analytical TLC was carried out on precoated plates (silica gel 60 F$_{254}$ from EM Science) and components were visualized with UV light and/or stained with iodine. Column chromatography was performed with silica gel 60 (70–230 mesh from EM Science). All chemical reagents and anhydrous solvents were purchased from Aldrich Chemical Co.

Example 1

General Procedures for Synthesis of Dialkyl Phosphonomethyltriflates

In this Example, a general method for synthesizing dialkyl phosphonomethyltriflates is provided based on a reported procedure.[19] This method has been applied in preparing representative dialkyl phosphonomethyltriflates 3a–c shown in Scheme 1.

To a stirred solution of dialkyl hydroxymethylphosphonate (30.6 mmol) and 2,6-lutidine (37.6 mmol) in anhydrous CH$_2$Cl$_2$ (50 mL) at −50° C. under N$_2$ was added trifluoromethanesulfonic anhydride (35.5 mmol) dropwise. The resulting mixture was allowed to warm to 0° C. over a period of 1.5 h, whereupon the dark brown solution was diluted with ether (300 mL). The precipitates formed were removed by filtration. The ethereal solution was successively washed with water, 1 N HCl, and brine and then dried over Na$_2$SO$_4$. After concentration, a yellow oil was obtained, which was used in the next step without further purification.

Diethyl Phosphonomethyltriflate (3a):[18] 9.0 g (98% yield). $^1$H NMR (CDCl$_3$) δ1.39 (t, J=7.1 Hz, 6 H), 4.27–4.24 (m, 4 H,), 4.64 (d, J=8.8 Hz, 2 H).

Dimethyl Phosphonomethyltriflate (3b): 4.9 g (67% yield). $^1$H NMR (CDCl$_3$) δ3.89 (d, J=8.3 Hz, 6 H), 4.65 (d, J=8.8 Hz, 2 H).

Dibenzyl Phosphonomethyltriflate (3c): 8.3 g (65% yield). $^1$H NMR (CDCl$_3$) δ4.45 (d, J=9.0 Hz, 2 H), 5.10 (m, 4 H), 7.34–7.39 (m, 10 H).

Example 2

General Procedure for Synthesis of Dialkylphosphonomethyl-triphenylphosphonium Triflates In this Example, a general method for synthesizing dialkyl phosphonomethyltriphenyl-phosphonium triflates is provided. This method has been applied in preparing representative dialkyl phosphonomethyltriphenylphosphium triflates (4a–c) shown in Scheme 1 and can be used to prepare a variety of other triflates such as dialkyl phosphonomethyltri(aryl, alkyl, or arylalkyl)phosphium triflates.

To a stirred solution of triphenylphosphine (34.4 mmol) in anhydrous CH$_2$Cl$_2$ (50 mL) was added dialkyl phosphonomethyltriflate (3a–c) (30 mmol) in anhydrous CH$_2$Cl$_2$ (15 mL) dropwise at 0° C. under N$_2$. The mixture was allowed to warm to room temperature and then stirred overnight (~16 h). The solvent was removed under reduced pressure to about one third of the volume and the remaining oil triturated with ether (200 mL). A white solid was formed and collected by filtration. After being washed with ether (50 mL x 2), dialkyl phosphonomethyltriphenylphosphonium triflates (4a–c) were obtained as white solids. The analytical samples were obtained by recrystallization from ethyl acetate/hexane.

Diethyl Phosphonomethyltriphenylphosphonium Triflate (4a): 13.7 g (82% yield). mp 98°–100° C. $^1$H NMR (CDCl$_3$) δ1.16 (t, J=7.1 Hz, 6 H), 3.90–4.10 (m, 4 H), 4.20 (dd, J=19.6, 16.1 Hz, 2 H), 7.65–7.90 (m, 15 H); MS (CI): 414 (26.1, M-CF$_3$SO$_3$H+2), 423 (100, M-CF$_3$SO$_3$H+1), 367 (26.1, M-CF$_3$SO$_3$H-C$_2$H$_5$O); IR (KBr, cm$^{-1}$): 1589, 1443, 1277, 1154, 1032; Anal. calcd. for C$_{24}$H$_{27}$F$_3$O$_6$P$_2$S: C, 51.25; H, 4.84; P, 11.01; S, 5.70. Found: C, 50.89; H, 4.84; P,10.67; S, 6.38.

Dimethyl Phosphonomethyltriphenylphosphonium Triflate (4b): 13.3 g (83% yield). mp 149°–151° C. $^1$H NMR (CDCl$_3$) δ3.62 (d, J=11.6 Hz, 6 H), 4.26 (dd, J=19.9, 16.1 Hz, 2 H), 7.65–7.88 (m, 15 H); IR (KBr, cm$^{-1}$): 1589, 1443, 1273, 1154, 1038; MS (CI): 386 (21.7, M-CF$_3$SO$_3$H+2), 385 (100, M-CF$_3$SO$_3$H+1), 353 (35.7, M-CF$_3$SO$_3$H-CH$_3$O); Anal. calcd. for C$_{22}$H$_{23}$F$_3$O$_6$P$_2$S: C, 49.44; H, 4.34; P, 11.59; S, 6.00. Found: C, 49.06; H, 4.23; P, 11.29; S, 6.19.

Dibenzyl Phosphonomethyltriphenylphosphonium Triflate (4c): 17.3 g (84% yield). mp 78°–81° C. $^1$H NMR (CDCl$_3$) δ4.30 (dd, J=20.1, 16.1 Hz, 2 H), 4.88 (m, 4 H), 7.17–7.79 (m, 25 H); IR (KBr, cm$^{-1}$): 1732, 1589, 1439, 1366, 1275, 1217, 1155, 1034; MS (FAB): 537 (100, M-CF$_3$SO$_3$H+1); Anal. calcd. for C$_{34}$H$_{31}$F$_3$O$_6$P$_2$S: C, 59.48; H, 4.55; P, 9.02; S, 4.67. Found: C, 59.48; H, 4.53; P, 8.59; S, 4.87.

Diethyl Phosphonomethyltributylphosphonium Triflate (4d): The compound 4d was synthesized by the procedure similar to that described above. Tri-n-butylphosphine, instead of triphenylphosphine, was used. From 1 g (33.3 mmol) of 3a and 0.8 g (40 mmol) of tri-n-butylphosphine, 1.1 g (72% yield) of a pale yellow oil was obtained. $^1$H NMR (CDCl$_3$) δ0.98 (t, J=7.0 Hz, 9 H), 1.38 (t, J=7.0 Hz, 6 H), 1.52 (m, 12 H), 2.37 (m, 6 H), 3.09 (dd, J=19.5, 15.7 Hz, 2 H), 4.21 (apparent quintet, J=7.2 Hz, 4 H); IR (KBr, cm$^{-1}$): 1467, 1395, 1262, 1155, 1022; MS(CI): 354 (30.2, M-CF$_3$SO$_3$H+2), 353 (100, M-CF$_3$SO$_3$H+1).

Diethyl Phosphonomethylidenetriphenylphosphorane (1b): To a stirred suspension of NaH (50 mg, 1.25 mmol, washed with hexane) in anhydrous THF (2 mL) was added triphenylphosphonium triflate salt (4a) (300 mg, 0.53 mmol) in anhydrous THF (2 mL) at 0° C. under $N_2$. The resulting mixture was stirred at 0° C. for 0.5 h. The solvent was then removed at reduced pressure and the residue extracted with anhydrous $CH_2Cl_2$. After concentration of the extracts, a colorless oil was obtained which was then triturated with hexane to yield an off-white solid (180 mg, 83% yield). An analytical sample was obtained by repetitive trituration with hexane: mp 73°–75° C. $^1$H NMR (CDCl$_3$) δ1.12 (t, J=7.1 Hz, 6 H), 1.27 (d, J=7.5 Hz, 1 H), 3.86 (apparent quintet, J=10.5 Hz, 4 H), 7.40–7.74 (m, 15 H); MS (CI): 414 (27.2, M+2), 413 (100, M +1), 412 (32.9, M$^+$), 367 (38.9, M-$C_2H_5O$); IR (KBr, cm$^{-1}$): 1587, 1483, 1433, 1204, 1101, 976; Anal. calcd. for $C_{23}H_{26}O_3P_2$: C, 66.99; H, 6.35; P, 15.02; Found: C, 67.25; H, 6.57; P, 14.75.

Diethyl Phosphonomethylidenetributylphosphorane (1c): The procedure used for preparation of 1b decribed above was followed for synthesis of 1c. Thus, from tributylphosphonium triflate salt (4d) (100 mg, 0.20 mmol) and NaH (20 mg, 0.40 mmol, washed with hexane) in anhydrous THF (2 mL), 60 mg (85% yield) of crude product was obtained which was used in the reaction with aldehydes without further purification. $^1$H NMR (CDCl$_3$) δ0.93 (t, J=7.0 Hz, 9 H), 1.30 (m, 7 H), 1.38 (m, 12 H), 1.78 (m, 6 H), 4.21 (m, 4 H).

Example 3

General Procedures for Synthesis of α,β-Unsaturated Phosphonate Esters

In this Example, two general procedures for synthesizing unsaturated α,β-unsaturated phosphonate esters are provided.

PROCEDURE A, Using Phosphonium Triflate Salt 4a or 4d: To a stirred solution of aldehyde (1.20 nunol) in anhydrous toluene (5 mL) and DMF (1 mL) was added diethyl phosphonomethyltriphenylphosphonium triflate 4a or 4d (1.80 mmol) at r.t under $N_2$, followed by addition of triethylamine (7.20 mmol). The resulting mixture was slowly heated to 100° C. (for 4a) and 70° C. (for 4d). The reaction was monitored by TLC analysis. After being stirred at that temperature for a period of time indicated in Table 1, the solvents were removed under reduced pressure and the residue chromatographed on a silica gel column, eluting with ethyl acetate/hexane (1:1) to afford the product. The ratio of cis and trans isomers was determined by $^1$H NMR.

PROCEDURE B, Using Ylide 1b or 1c: The reaction was carried out using a procedure similar to that described above. However, toluene was used as the solvent without addition of triethylamine.

Diethyl 2-Phenylethenephosphonate (5a): colorless liquid. $^1$H NMR (CDCl$_3$) δ for cis isomer (minor): 1.18 (t, J=7.1 Hz, 6 H), 4.00 (apparent quintet, J=7.2 Hz, 4 H), 5.81 (dd, J=15.8, 12.3 Hz, 1 H), 7.15–7.75 (m, 6 H); δ for trans isomer (major):[25] 1.36 (t, J=7.1 Hz, 6 H), 4.14 (apparent quintet, J=7.3 Hz, 4 H), 6.26 (apparent t, J=17.5 Hz, 1 H), 7.15–7.75 (m, 6 H); IR (neat, cm$^{-1}$): 1617, 1246, 1053, 1028; MS (CI): 242 (12.0, M+2), 241 (100, M$^+$).

Diethyl 2-(4-Chlorophenyl)ethenephosphonate (5b): colorless liquid. $^1$H NMR (CDCl$_3$) δ for cis isomer (minor): 1.20 (t, J=7.0 Hz, 6 H), 4.00 (apparent quintet, J=7.1 Hz, 4 H), 5.81 (apparent t, J=15.2 Hz, 1 H), 7.10–7.65 (m, 5 H); δ for trans isomer (major): 1.34 (t, J=7.2 Hz, 6 H), 4.12 (apparent quintet, J=7.0 Hz, 4 H), 6.22 (apparent t, J=17.3 Hz, 1 H), 7.10–765 (m, 5 H); IR (neat, cm$^{-1}$): 1618, 1246, 1053, 1028; MS (CI): 277 and 275 (31.4, 100, M+1), 276 and 274 (4.8, 13.4, M$^+$).

Diethyl 2-(4-Methoxyphenyl)ethenephosphonate (5c): colorless liquid. $^1$H NMR (CDCl$_3$) δ for cis isomer (minor): 1.23 (t, J=7.1 Hz, 6 H), 3.83 (s, 3 H), 4.03 (apparent quintet, J=7.3 Hz, 4 H), 5.65 (apparent t, J=14.9 Hz, 1 H), 6.90–7.55 (m, 5 H); δ for trans isomer (major): [22]1.35 (t, J=7.1 Hz, 6 H), 3.83 (s, 3 H), 4.13 (apparent quintet, J=7.1 Hz, 4 H), 6.09 (apparent t, J=18.2 Hz, 1 H), 6.90–7.55 (m, 5 H); IR (neat, cm$^{-1}$): 1605, 1258, 1175, 1030; MS (CI): 272 (26.2, M+2), 271 (100, M+1), 270 (19.0, M$^+$).

Diethyl 1,2-cis-3,4-trans-4-Phenylbuta-1,3-dienephosphonate (cis-5d): pale yellow liquid. $^1$H NMR (CDCl$_3$) δ1.36 (t, J=7.1 Hz, 6 H), 4.13 (apparent quintet, J=7.1 Hz, 4 H), 5.58 (dd, J=17.4, 12.5 Hz, 1 H), 6.78 (d, J=15.4 Hz, 1 H), 7.02 (dt, J=50.7, 12.2 Hz, 1 H), 7.3–7.5 (m, 5 H), 7.82 (ddt, J=15.0, 11.9, 1.5 Hz, 1 H)); UV (MeOH) $\lambda_{max}$ 297 (38,800) nm; IR (neat, cm$^{-1}$): 1626, 1584, 1244, 1051, 1026; MS (CI): 268 (18.8, M+2), 267 (100, M+1), 266 (9.0, M$^+$).

Diethyl 1,2,3,4-trans-4-Phenylbuta-1,3-dienephosphonate (trans-5d): pale yellow liquid. $^1$H NMR (CDCl$_3$) δ1.35 (t, J=7.1 Hz, 6 H), 4.12 (apparent quintet, J=7.2 Hz, 4 H), 5.80 (dd, J=18.9, 16.7 Hz, 1 H), 6.84 (m, 2 H), 7.16–7.46 (m, 6 H); UV (MeOH) $\lambda_{max}$294 (43,400) nm; IR (neat, cm$^{-1}$): 1626, 1589, 1244, 1054, 1022; MS (CI): 268 (34.2, M+2), 267 (100, M+1), 266 (29.1, M$^+$).

Diethyl trans-3-Phenyl-2-propenephosphonate (5e): colorless liquid. $^1$H NMR (CDCl$_3$) δ1.32 (t, J=7.1 Hz, 6 H), 2.77 (ddd, J=22.2, 7.6, 1.1 Hz, 2 H,), 4.12 (apparent quintet, J=7.3 Hz, 4 H), 6.15 (apparent dq, J=14.9, 7.2 Hz, 1 H), 6.53 (dd, J=15.8, 5.1 Hz, 1 H), 7.22–7.40 (m, 5 H); $^{13}$C NMR (CDCl$_3$) δ16.3 (d, $^3J_{C,P}$=5.7 Hz), 31.0 (d, $^1J_{C,P}$=140.9 Hz), 62.0 (d, $^2J_{C,P}$=6.9 Hz), 118.8 (d, $^2J_{C,P}$=12.6 Hz), 127.6 and 128.6 (2 s), 134.7 (d, $^3J_{C,P}$=14.9 Hz), 136.9 (d, $^4J_{C,P}$=3.4 Hz); IR (neat, cm$^{-1}$): 1651, 1599, 1250, 1024; MS (CI): 256 (13.7, M+2), 255 (100, M+1), 254 (29.1, M$^+$).

Diethyl 1-Hexenephosphonate (5f): colorless liquid. $^1$H NMR (CDCl$_3$) δ for cis isomer (minor): 0.91 (t, J=7.0 Hz, 3 H), 1.31 (t, J=7.1 Hz, 6 H), 1.24–1.45 (m, 4 H), 2.52 (m, 2 H), 4.07 (apparent quintet, J=7.3 Hz, 4 H), 5.58 (dd, J=19.9, 13.0 Hz, 1 H), 6.47 (ddt, J=53.0, 13.0, 7.6 Hz, 1 H); δ for trans isomer (major): 0.89 (t, J=7.0 Hz, 3 H), 1.31 (t, J=7.1 Hz, 6 H), 1.24–1.45 (m, 4 H), 2.21 (m, 2 H), 4.06 (apparent quintet, J=7.3 Hz, 4 H), 5.63 (dd, J=21.2, 17.1 Hz, 1 H), 6.78 (ddt, J=22.0, 17.1, 6.7 Hz, 1 H); IR (neat, cm$^{-1}$): 1632, 1248, 1028; MS (CI): 222 (13.2, M+2), 221 (100, M+1).

Diethyl 2-(4-Chlorophenyl)-3,3,3-trifluoro-1-propenephosphonate (5 g): colorless liquid. $^1$H NMR (CDCl$_3$) δ for Z- isomer (major): 1.17 (t, J=7.1 Hz, 6 H), 3.78–4.01 (m, 4 H), 6.55 (dq, J=12.3, 1.2 Hz, 1 H), 7.36, 7.40 (AB type, $J_{AB}$=8.6 Hz, 4 H); δ for E- isomer (minor): 1.38 (t, J=7.1 Hz, 6 H), 4.22 (dq, J=7.2, 7.4 Hz, 4 H), 6.27 (d, J=8.4 Hz, 1 H), 7.35, 7.37 (AB type, $J_{AB}$=8.4 Hz, 4 H); IR (neat, cm$^{-1}$): 1643, 1595, 1256, 1134 and 1024; MS (CI): 345 and 343 (33.3, 100, M+1).

Example 4

Preparation of 9-[5,6-Dideoxy-6-diethylphosphono-2,3-O-isopropylidene-β-D-ribo-hex-5-enofuranosyl] adenine (6):

In this Example, the α,β-unsaturated phosphonate ester of 2',3'-isopropylideneadenosine was prepared using Procedure B of Example 3.

To a stirred solution of 2',3'-isopropylideneadenosine (200 mg, 0.65 mmol) and pyridinium trifluoroacetate (62 mg, 0.32 mmol) in dry DMSO (5 mL) at room temperature under $N_2$ was added a solution of DCC (400 mg, 1.95 mmol) in dry DMSO (1 mL). The reaction mixture was stirred at room temperature for 8 h, and then additional DCC (300 mg, 1.46 mmol) and pyridinium trifluoroacetate (38 mg, 0.20 mmol) was added. The reaction was stirred overnight and TLC analysis indicated the completion of the reaction. After removal of the resulting DCU by filtration, crude 1b (400 mg, 0.98 mmol) was added into the filtrate. The resulting mixture was stirred at r.t for 36 h and then diluted with ethyl acetate (50 mL), washed with water (3×30 mL), dried over $Na_2SO_4$. A pale brown solid (71 mg, 25% yield) was obtained after silica gel column chromatography and elution with 5% methanol in $CH_2Cl_2$. mp 85°–89° C., $^1H$ NMR (DMSO-$d_6$) δ1.15 (t, J=6.9 Hz, 3H), 1.16 (t, J=7.1 Hz, 3 H) 135 (s, 3 H) 1.56 (s, 3 H), 3.82 (apparent quintet, J=7.8 Hz, 4 H), 4.81 (br, 1 H), 5.19 (dd, J=6.3 Hz, J=3.3 Hz, 1 H), 5.56 (d, J=5.7 Hz, 1 H), 5.72 (t, J=18.6 Hz, 1 H), 6.28 (s, 1 H), 6.65 (ddd, J=22.2 Hz, J=16.7 Hz, J=5.6 Hz, 1 H), 7.35 (s, 2 H), 8.15 and 8.30 (2 s, 2 H); IR(KBr, $cm^{-1}$): 3337 (m, $NH_2$), 1642, 1597, 1211, 1028; MS (CI) 441 (213, M+2), 440 (100, M+1), 439 (2.5, $M^+$).

Example 5

Diethyl 3-Phenylpropylphosphonate (7a):

In this Example, the saturated phosphonate ester derivative of diethyl 2-phenylethenephosphonate (5a) was prepared via hydrogenation.

A solution of compound 5e (30 mg) in ethanol (5 mL) was hydrogenated over 10% Pd/C (5 mg) at atmospheric pressure. The mixture was vigorously stirred at r.t for 3 h, whereupon the catalyst was removed by filtration and the filtrate concentrated under reduced pressure to afford 7a as a colorless oil (30 mg, 99% yield). $^1H$ NMR (CDCl$_3$) δ1.30 (t, J=7.1 Hz, 6 H), 1.69–1.77 (m, 2 H), 1.91–1.94 (m, 2 H), 2.69 (t, J=7.5 Hz, 2 H), 4.04–4.10 (m, 4 H), 7.16–7.30 (m, 5 H).

Example 6

Diethyl 2-Phenylethylphosphonate (7b):

Compound 5a (30 mg) was hydrogenated using the same procedure described in Example 5 to afford 7b quantitatively. $^1H$ NMR (CDCl$_3$) δ1.32 (t, J=7.1 Hz, 6 H), 2.11 (m, 2 H), 2.85 (m, 2 H), 4.09 (apparent quintet, J=7.4 Hz, 4 H), 7.21–7.29 (m, 5 H).

Example 7

2-(4-Chlorophenyl)ethenephosphonic acid (8):

In this Example, the phosphonic acid derivative of diethyl 2-(4-chlorophenyl) ethenephosphonate 5b was prepared via reaction of 5b with bromotrimethylsilane.

To a stirred solution of 5b (50 mg, 0.18 mmol) in dry $CH_2Cl_2$ (5 mL) at r.t under $N_2$ was added bromotrimethylsilane (280 mg, 1.8 mmol) dropwise. The reaction mixture was stirred for 2 h. The volatile materials were then removed under vacuum and the residue dissolved in water (5 mL) and stirred for 10 min. The aqueous solution was washed with ether and co-evaporated with MeOH to dryness, affording a white solid (42 mg, 94% yield). mp>300° C.; $^1H$ NMR ($D_2O$) δ for cis isomer (minor): 6.03 (dd, J=14.4, 10.5 Hz, 1 H), 6.81 (dd, J=40.5, 14.4 Hz, 1 H), 7.38, 7.79 (AB type, $J_{AB}$=8.7 Hz, 4 H); δ for trans isomer (major): 6.54 (dd, J=17.7, 13.5 Hz, 1 H), 6.99 (t, J=18.2 Hz, 1 H), 7.41, 7.53 (AB type, $J_{AB}$=8.7 Hz, 4 H); IR (KBr, $cm^{-1}$): 3424, 1665, 1491, 1368, 1090, 978; MS (FAB): 219 and 217 (39.0, 100, $M^+$).

References

1. Engel, R. Chem Rev. 1977, 77, 349.
2. Klachbum G. M.; Perree, T. D.; Rashid, A.; Bisbal, C.; Lebleu, B. Chem. Scr. 1986, 26, 21.
3. Kafarski, P.; Lejczak, B. Phosphorus, Sulfur, Silicon, Relat. Elem. 1991, 63, 193.
4. O'Donnell, M. J.; Lawley, L. K.; Pushpavanam, P. B.; Burger, A.; Bordwell, F. G.; Zhang, X.-M. Tetrahedron Lett. 1994, 35, 6421 and references cited therein.
5. Wadsworth, W. S., Jr. Org. React. 1977, 25, 73.
6. Maryanoff, B. E.; Reitz, A. B. Chem. Rev. 1989, 89, 863.
7. Minami, T.; Motoyoshiya, J. Synthesis 1992, 333.
8. Bhattacharya, A.; Thyagarajan, G. Chem. Rev. 1981, 81, 415.
9. Jones, G. H.; Hamamura, E. K.; Moffatt, J. G. Tetrahedron Lett. 1968, 5731.
10. Jones, G. H.; Moffatt, J. G. J Am. Chem. Soc. 1968, 90, 5337.
11. Fuertes, M.; Witkowski, J. T.; Streeter, D. G.; Robins, R. K. J Med. Chem. 1974, 17, 642.
12. Kappler, F.; Hai, T. T.; Cotter, R. J.; Hyver, K. J.; Hampton, A. J Med. Chem. 1986, 29.
13. Martin, J. C.; Verheyden, J. P. H. Nucleosides Nucleotides 1988, 7, 365.
14. Secrist, J. A., III; Riggs, R. M.; Comber, R. N.; Montgomery, J. A. Nucleosides Nucleotides 1992, 11, 947.
15. Freeman, G. A.; Rideout, J. L.; Miller, W. H.; Reardon, J. E. J. Med. Chem., 1992, 35, 3192.
16. Gupta, A.; Sacks, K.; Khan, S.; Tropp, B. E.; Engel, R. Synthetic Commun. 1980, 10, 299.
17. Stang, P. J.; Hanack, M.; Subramanian, L. R. Synthesis 1982, 85.
18. Phillion, D. P.; Andrew, S. S. Tetrahedron Lett. 1986, 27, 1477.
19. Creary, X.; Underiner, T. L. J Org. Chem. 1985, 50, 2165.
20. Holy, A.; Rosenberg, I. Coll. Czech. Chem. Commun. 1982, 47, 3447.
21. Krecmerova, M.; Hrebabecky, H.; Holy, A. Coll. Czech. Chem. Commun. 1990, 55, 2521.
22. Kenyon, G. L.; Westheimer, F. H. J Am. Chem. Soc. 1966, 88, 3557.
23. Petrov, A. A.; Ionin, B. I.; Ignatyev, V. M. Tetrahedron Lett. 1968, 15.
24. Tavs, P.; Weitkamp, H. Tetrahedron 1970, 26, 5529.
25. Xu, Y.; Jin, X.; Huang, G.; Huang, Y. Synthesis 1983, 556.

What we claim:

1. A compound of formula:

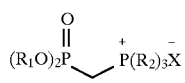

wherein X represents triflate, halide, $BF_4$, $SbF_6$, or $ClO_4$; $R_1$ represents alkyl, aryl or arylalkyl; and $R_2$ represents alkyl, aryl or arylalkyl, provided that $R_1$ and $R_2$ not represent phenyl at the same time and that $R_1$ not represent aryl when X is halide.

2. A compound according to claim 1, wherein $R_1$ represents methyl, ethyl, or benzyl.

3. A compound according to claim 1, wherein $R_2$ represents n-butyl or phenyl.

4. A compound according to claim 1, wherein X represents triflate.

5. A method for preparing a compound of formula I:

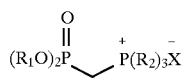

wherein X represents triflate, halide, $BF_4$, $SbF_6$, $ClO_4$; $R_1$ represents alkyl, aryl or arylalkyl; and $R_2$ represents alkyl, aryl or arylalkyl, said method comprising reacting $(R_2)_3P$ with a compound of formula III

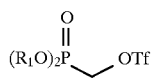

wherein $R_1$ represents alkyl, aryl or arylalkyl and wherein $R_2$ is defined above.

6. A method for preparing a compound of formula II:

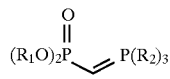

wherein $R_1$ represents alkyl, aryl or arylalkyl; and $R_2$ represents alkyl, aryl or arylalkyl, said method comprising reacting a compound of formula I:

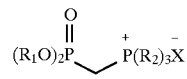

wherein X represents triflate, halide, $BF_4$, $SbF_6$, or $ClO_4$; R. represents alkyl, aryl or arylalkyl; and $R_2$ represents alkyl, aryl or arylalkyl, with a base under anhydrous conditions.

* * * * *

UNITED STATES PATENT AND TRADEMARK OFFICE
CERTIFICATE OF CORRECTION

PATENT NO. : 5,852,198
DATED : Dec. 22, 1998
INVENTOR(S) : Y. Xu, et al

It is certified that error appears in the above-identified patent and that said Letters Patent is hereby corrected as shown below:

On the Title page, item [75], delete "both" and insert -- ; Ze-Qi Xu, Naperville, all --;

On the Title page, item [73], delete "Medichem" and insert -- MediChem --;

On the Title page, item [56], delete "Xu, Y.; jin, X.; Huang, G.; Huang, Y. *Synthesis*, 1983, 556." and insert -- Xu, Y.; Jin, X.; Huang, G.; Huang, Y. *Synthesis*, Jul. 1983, 556. --;

On the Title Page, item [57], first paragraph, third sentence delete "phosphono-methylidenetriphenylphosphorane" and insert -- phosphonomethylidenetriphenylphosphorane --;

In Column 2, line 29, between "well" and "their" insert -- as --;

In Column 4, line 25, delete "C." and insert -- C --;

In Table 1, Entry 1, delete "PhCH=CHP(O)(Oet)$_2$(5a)(70:30)" and insert -- PhCH=CHP(O)(OEt)$_2$(5a)(70:30) --;

UNITED STATES PATENT AND TRADEMARK OFFICE
CERTIFICATE OF CORRECTION

PATENT NO.   : 5,852,198
DATED        : Dec. 22, 1998
INVENTOR(S)  : Y. Xu, et al

It is certified that error appears in the above-identified patent and that said Letters Patent is hereby corrected as shown below:

In Table 1, Entry 7, delete "Ph(CH=CH)2P(O)(OEt)$_2$(5d)(60:40)" and insert

-- Ph(CH=CH)$_2$P(O)(OEt)$_2$(5d)(60:40) --;

In Table 1, footnote $^c$, delete "1H" and insert -- $^1$H --;

In Col. 6, line 7, delete "a" and insert -- $\alpha$ --;

In Col.6, line 25, delete "a,," and insert -- $\alpha,\beta$ --;

In Col. 7, line 33, delete "$\delta$ppm" and insert -- $\delta$ ppm --;

In Col. 7, line 53, delete "C." and insert -- C --;

In Col. 7, line 55, delete "C." and insert -- C --;

In Col. 8, line 8, delete "Dialkylphosphonomethyl-triphenylphosphonium" and insert -- Dialkylphosphonomethyltriphenylphosphonium --;

UNITED STATES PATENT AND TRADEMARK OFFICE
CERTIFICATE OF CORRECTION

PATENT NO. : 5,852,198
DATED : Dec. 22, 1998
INVENTOR(S) : Y. Xu, et al

It is certified that error appears in the above-identified patent and that said Letters Patent is hereby corrected as shown below:

In Col. 8, line 11, delete "phosphonomethyltriphenyl-phosphonium" and insert -- phosphonomethyltriphenylphosphonium --;

In Col. 8, line 21, delete "C." and insert -- C --;

In Col. 9, line 5, delete "C." and insert -- C --;

In Col. 9, line 6, delete "C." and insert -- C --;

In Col. 9, line 49, insert a comma between "(1:1)" and "to";

In Col. 10, line 40, delete "'H" and insert -- $^1$H --;

In Col. 11, line 16, delete "C." and insert -- C --;

In Col. 12, reference 10, insert a period after the "J" in "J Am. Chem. Soc.";

In Col. 12, reference 11, insert a period after the "J" in "J Med. Chem.";

UNITED STATES PATENT AND TRADEMARK OFFICE
CERTIFICATE OF CORRECTION

PATENT NO. : 5,852,198
DATED : Dec. 22, 1998
INVENTOR(S) : Y. Xu, et al

It is certified that error appears in the above-identified patent and that said Letters Patent is hereby corrected as shown below:

In Col. 12, reference 12, insert a period after the "J" in "J Med. Chem.";

In Col. 12, reference 19, insert a period after the "J" in "J Org. Chem.";

In Col. 12, reference 22, insert a period after the "J" in "J Am. Chem. Soc.";

In Col. 14, line 21, delete "R." insert -- $R_1$ --.

Signed and Sealed this

Tenth Day of August, 1999

Q. TODD DICKINSON

Attest:

Attesting Officer

Acting Commissioner of Patents and Trademarks